(12) United States Patent
Martin

(10) Patent No.: US 8,881,635 B2
(45) Date of Patent: Nov. 11, 2014

(54) VARIABLE DENIER YARN AND SUTURE

(75) Inventor: Daniel L. Martin, Palo Alto, CA (US)

(73) Assignee: Syntorr Inc., Palo Alto, CA (US)

(*) Notice: Subject to any disclaimer, the term of this patent is extended or adjusted under 35 U.S.C. 154(b) by 178 days.

(21) Appl. No.: 13/354,204

(22) Filed: Jan. 19, 2012

(65) Prior Publication Data

US 2012/0197294 A1 Aug. 2, 2012

Related U.S. Application Data

(60) Provisional application No. 61/438,880, filed on Feb. 2, 2011, provisional application No. 61/453,453, filed on Mar. 16, 2011, provisional application No. 61/542,990, filed on Oct. 4, 2011.

(51) Int. Cl.
| | |
|---|---|
| *D04C 1/12* | (2006.01) |
| *D04B 21/20* | (2006.01) |
| *D04B 1/22* | (2006.01) |
| *A61B 17/06* | (2006.01) |
| *A61B 17/00* | (2006.01) |

(52) U.S. Cl.
CPC ............ *A61B 17/06166* (2013.01); *D04C 1/12* (2013.01); *D04B 21/202* (2013.01); *A61B 2017/00526* (2013.01); *D04B 1/22* (2013.01); *D10B 2509/04* (2013.01)
USPC ....................................... 87/6; 87/8

(58) Field of Classification Search
USPC ............................. 87/6, 8, 9, 11, 13; 606/228
See application file for complete search history.

(56) References Cited

U.S. PATENT DOCUMENTS

| | | | |
|---|---|---|---|
| 1,860,030 | A | 5/1932 | Hinchliff |
| 2,020,197 | A | 11/1935 | Franz |
| 2,064,074 | A | 12/1935 | James |
| 2,213,720 | A | 9/1940 | Franz |
| 2,257,953 | A * | 10/1941 | Haskell ............................... 87/6 |
| 3,357,171 | A | 12/1967 | Marshall |
| 3,568,277 | A | 3/1971 | Mattingly |

(Continued)

FOREIGN PATENT DOCUMENTS

| | | |
|---|---|---|
| JP | 07324242 A | 12/1995 |
| JP | 09031783 | 2/1997 |
| JP | 10280238 | 10/1998 |
| JP | 2004149940 | 5/2004 |

OTHER PUBLICATIONS

Fontanazza, Maria; Expanding Medical Textiles: Q&A with Biomedical Structures CEO Dean Tulumaris; published on Orthotec (http://www.orthotec.com) on Jan. 9, 2012, 4 pages.

*Primary Examiner* — Shaun R Hurley
(74) *Attorney, Agent, or Firm* — Shay Glenn LLP

(57) ABSTRACT

A textile yarn includes a first segment and a second segment. The first segment includes a plurality of first strands and has a substantially constant first denier. The second segment includes a plurality of second strands integrated together and has a substantially constant second denier. There are more second strands in the second segment than first strands in the first segment such that the second denier is greater than the first denier. A first portion of the plurality of second strands is made from a first plurality of yarn elements that extend through the first and second segments. A second portion of the plurality of second strands is made from a second plurality of yarn elements present in the second segment and not the first segment. The yarn elements in the second plurality of yarn elements terminate in a transition zone between the first segment and the second segment.

15 Claims, 21 Drawing Sheets

(56) References Cited

U.S. PATENT DOCUMENTS

| | | |
|---|---|---|
| 3,568,278 A | 3/1971 | Mattingly |
| 3,587,221 A | 6/1971 | Buzano |
| 3,738,125 A | 6/1973 | Blezard et al. |
| 3,748,874 A | 7/1973 | Blezard |
| 4,321,854 A * | 3/1982 | Foote et al. .................. 87/6 |
| 4,621,638 A | 11/1986 | Silvestrini |
| 5,341,632 A | 8/1994 | Jung et al. |
| 5,645,568 A | 7/1997 | Chervitz et al. |
| 6,134,923 A | 10/2000 | Lay et al. |
| 6,716,234 B2 | 4/2004 | Grafton et al. |
| 7,329,271 B2 | 2/2008 | Koyfman et al. |
| 7,845,262 B2 * | 12/2010 | Ueda .................. 87/6 |
| 2002/0029066 A1 | 3/2002 | Foerster |
| 2005/0192631 A1 | 9/2005 | Grafton |
| 2006/0155328 A1 | 7/2006 | Foerster |
| 2007/0213770 A1 | 9/2007 | Dreyfuss |

\* cited by examiner

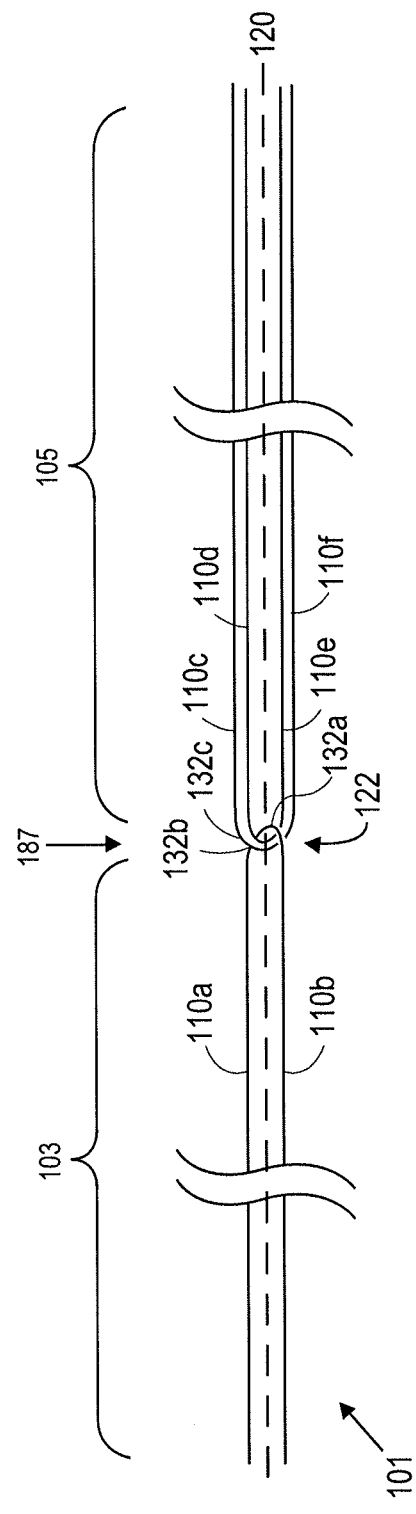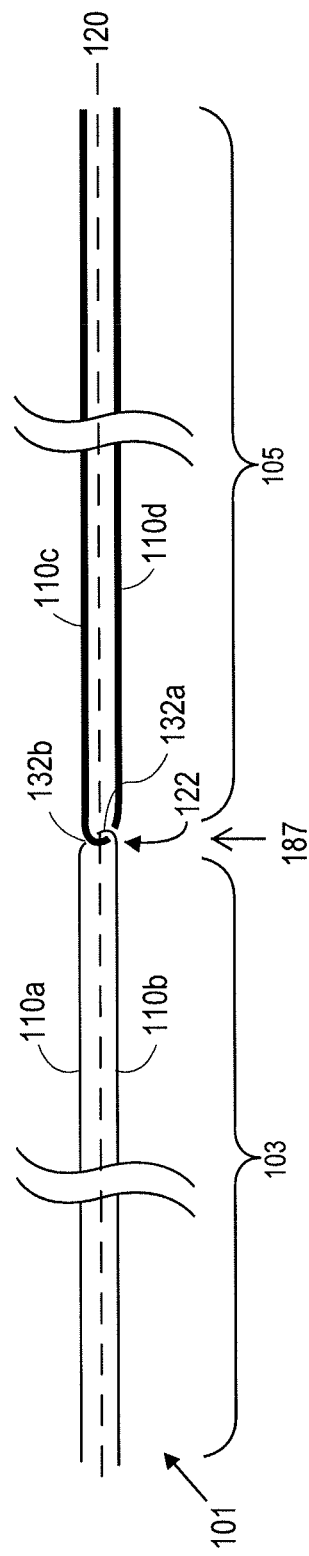
FIG. 1A
FIG. 1B

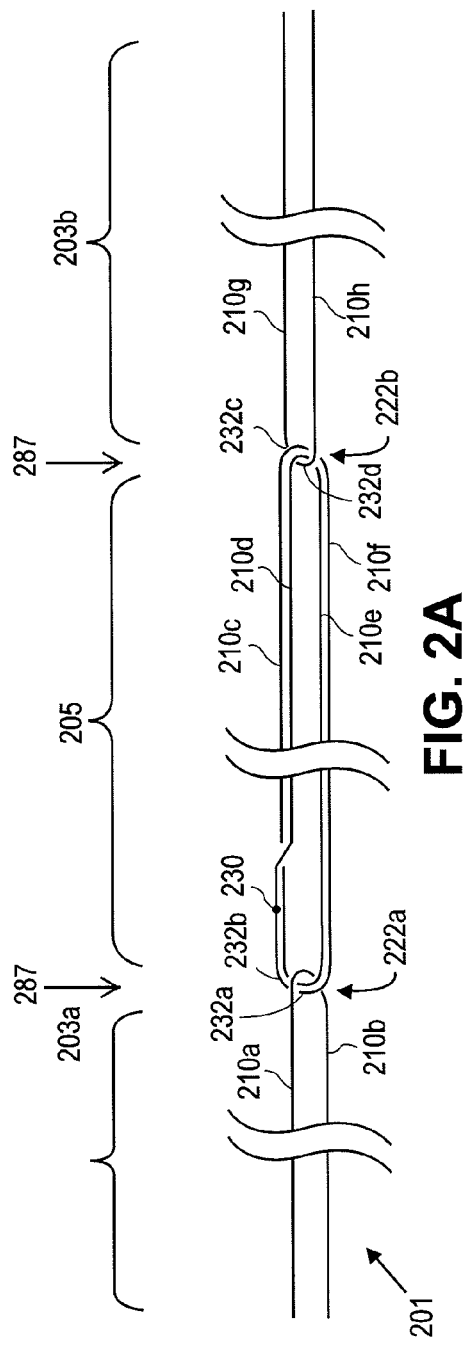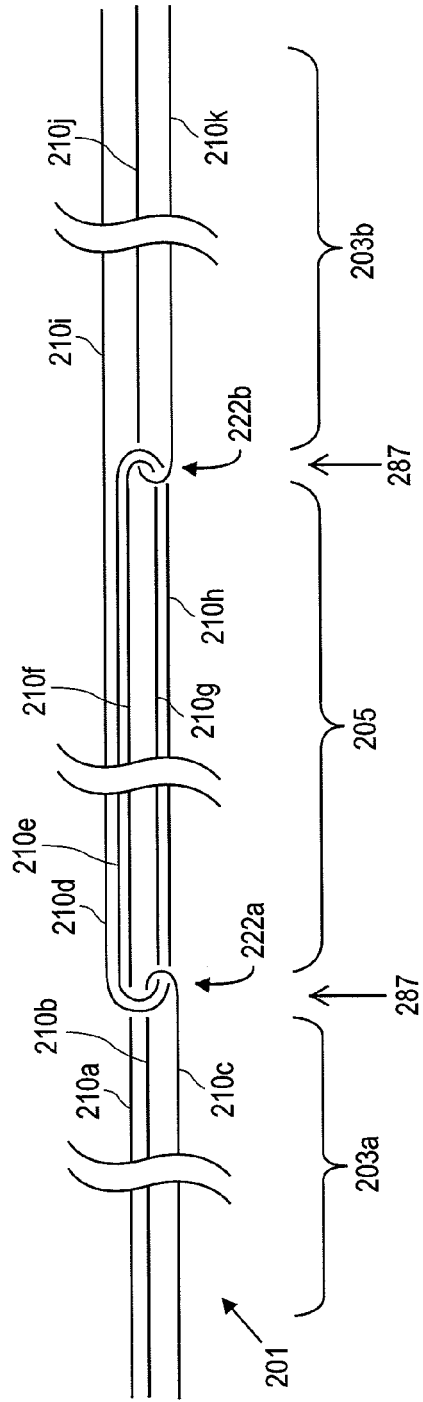

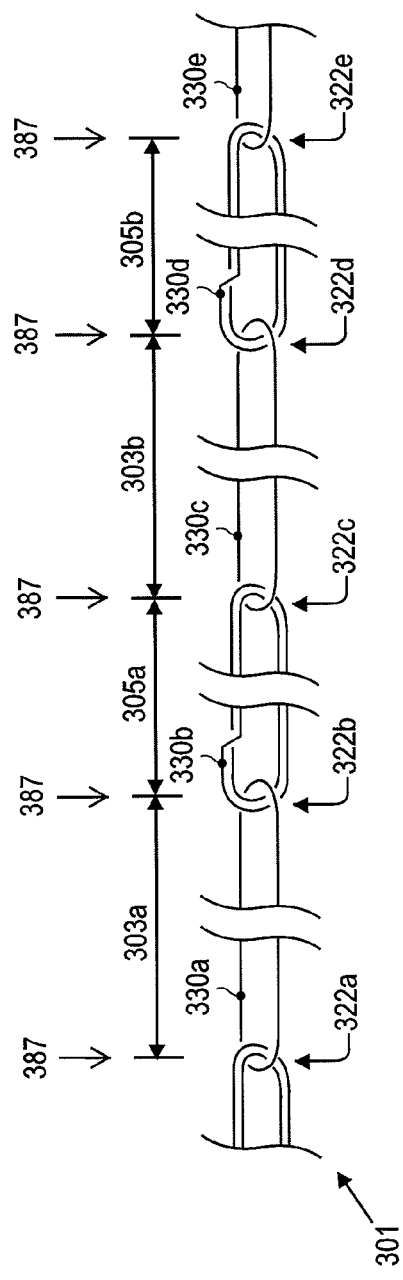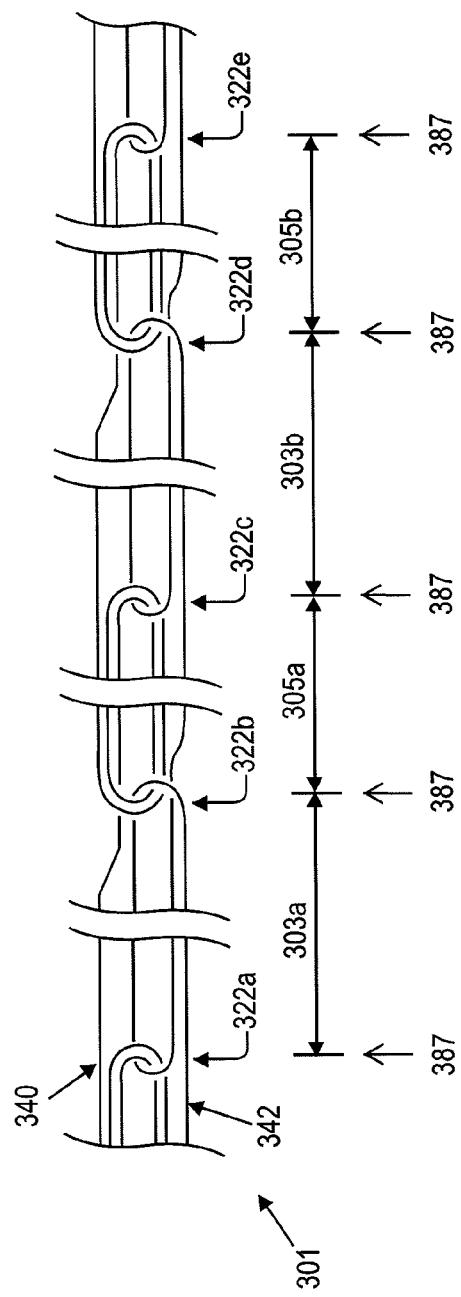

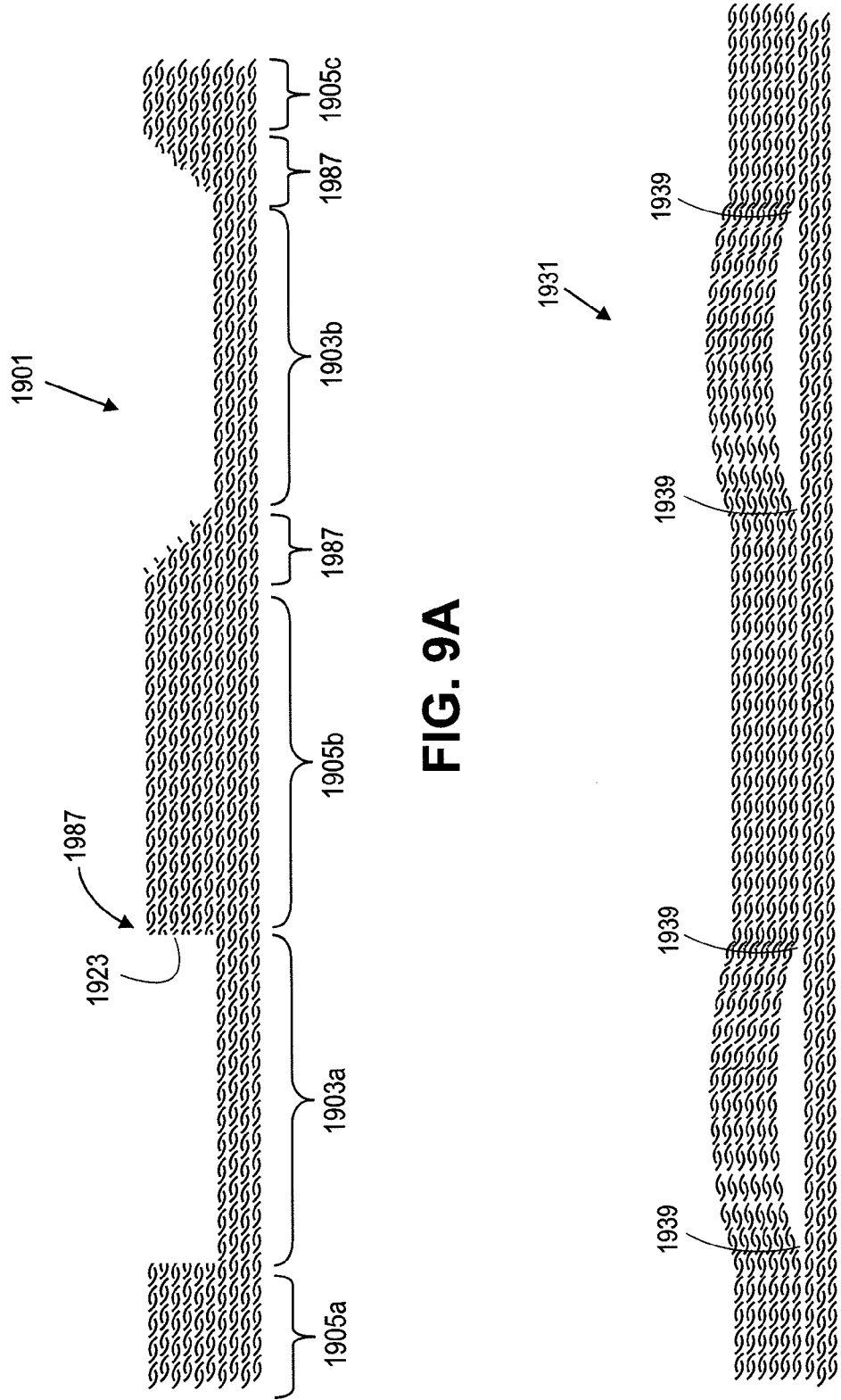

VARIABLE DENIER YARN AND SUTURE

CROSS REFERENCES TO RELATED APPLICATIONS

This application claims priority to U.S. Provisional Application No. 61/438,880, filed Feb. 2, 2011, titled "Variable Denier Yarn and Suture." This application also claims priority to U.S. Provisional Application No. 61/453,453, filed Mar. 16, 2011, titled "Variable Denier Yarn and Suture." This application also claims priority to U.S. Provisional Application No. 61/542,990, filed Oct. 4, 2011, titled "Variable Denier Surgical Suture and Braided Arborized Vascular Graft."

All of the above referenced applications are incorporated herein by reference in their entireties.

INCORPORATION BY REFERENCE

All publications and patent applications mentioned in this specification are herein incorporated by reference to the same extent as if each individual publication or patent application was specifically and individually indicated to be incorporated by reference.

FIELD

This application relates generally to variable denier yarn. In particular, this application relates to variable denier yarn that can be used to create a variable denier suture.

BACKGROUND

In many surgical procedures, particularly minimally invasive surgical procedures such as endoscopic suturing of internal body tissue, suturing must be accomplished using a suture that can fit through a surgical instrument or implant having a very small opening. If the opening has a circular cross-section, for example, threading a suture having the same diameter as the opening can be nearly impossible. Moreover, many surgical procedures require looping the suture and pulling a doubled suture through the opening. As a result, most sutures have a smaller denier so as to easily fit through the intended opening and/or so as to be able to be folded over for proper threading by drawing a loop of suture through the opening.

However, in many cases, a suture having the largest diameter possible for the intended opening is advantageous both because a large diameter suture will provide increased stability of the suture in tissue, a larger suture is stronger, and because space in the surgical device will not be wasted with a partially unfilled opening. Moreover, in certain cases, in order to properly pinch or otherwise restrain the suture to avoid movement of the suture after completion of the surgical process, the suture ideally fills a majority of the opening of the surgical instrument or implant.

Accordingly, there is a need for a suture having a larger denier at the central portion and a smaller denier near at least one end.

SUMMARY OF THE DISCLOSURE

In general, in one embodiment, a textile yarn includes a first segment and a second segment. The first segment includes a plurality of first strands and has a substantially constant first denier. The second segment includes a plurality of second strands integrated together and has a substantially constant second denier. There are more second strands in the second segment than first strands in the first segment such that the second denier is greater than the first denier. A first portion of the plurality of second strands is made from a first plurality of yarn elements that extend through the first segment and the second segment. A second portion of the plurality of second strands is made from a second plurality of yarn elements that are present in the second segment and not the first segment. The yarn elements in the second plurality of yarn elements terminate in a transition zone between the first segment and the second segment.

This and other embodiments can include one or more of the following features. The plurality of second strands can be braided together. The plurality of first strands can be braided together. The plurality of first strands can be braided together in a tubular braid, and the plurality of second strands can be braided together in a tubular braid. The plurality of first strands can be braided together in a flat braid, and the plurality of second strands can be braided together in a tubular braid. The plurality of first strands can be braided together in a flat braid, and the plurality of second strands can be braided together in a flat braid. The plurality of second strands can be integrated as a warp knit. The plurality of first strands can extend in parallel along the length of the first segment. All of the plurality of first strands can be made from the yarn elements extending through the first segment and the second segment. Ends of the strands in the second plurality of yarn elements can be loose in the transition zone. The second denier can be at least twice as large as the first denier. The textile yarn can be a suture. There can be a tubular over-braid running the length of the textile yarn. There can be a plurality of first segments and a plurality of second segments, and the first and second segments can be arranged in an alternating pattern along the length of the textile yarn. There can be a third segment, and there can be more third strands in the third segment than second strands in the second segment such that the third denier is greater than the second denier. A first portion of the plurality of third strands can be made from the same yarn elements as at least some of the plurality of first strands and at least some of the plurality of second strands. The first portion of the plurality of third strands can extend through the first, second, and third segments.

In general, in one embodiment, a textile yarn includes a first segment, a second segment, and a transition zone between the first segment and the second segment. The first segment includes a plurality of first strands coextending axially and has a substantially constant first denier. The second segment has a plurality of second strands coextending axially and has a substantially constant second denier. The second segment has a greater number of strands than the first segment such that the second denier is greater than the first denier. The transition zone includes a first loop formed by two first strands connected to a plurality of second loops, and each second loop is formed by two second strands, such that the transition zone has an increasing denier from the first segment to the second segment. The aspect ratio of the length of each segment and the width of a first strand or a second strand is greater than 100.

This and other embodiments can include one or more of the following features. The first loop can be directly connected to the plurality of second loops. The transition zone can further include a plurality of third loops connecting the first loop and the plurality of second loops. There can be a plurality of first segments or second segments and a plurality of transition zones, and the distance between each transition zone can be between 5 and 100 cm. The second segment can have a greater number of wales per course than the first segment. The second denier can be at least twice as large as the first denier. There can be a tubular over-braid running the length of the textile yarn. The textile yarn can be a suture.

In general, in one embodiment, a method of suturing includes threading a first segment through an opening of a surgical instrument and pulling the suture through tissue to place a second segment of the suture against soft tissue. The first segment includes a plurality of first strands and has a substantially constant first denier. The second segment includes a plurality of second strands integrated together and has a substantially constant second denier. There are more second strands in the second segment than first strands in the first segment such that the second denier is greater than the first denier. A first portion of the plurality of second strands is made from a first plurality of yarn elements that extend through the first segment and the second segment. A second portion of the plurality of second strands is made from a second plurality of yarn elements that are present in the second segment and not the first segment. The yarn elements in the second plurality of yarn elements terminate in a transition zone between the first segment and the second segment.

This and other embodiments can include one or more of the following features. The method can further include wrapping the first segment around a traction loop before threading the suture. The method can further include cutting the first segment of the suture after the suture is pulled through. The denier of the second segment can be at least twice the denier of the first segment.

In general, in one embodiment, a method of suturing including threading a first segment of a suture through an opening of a surgical instrument and pulling the suture through tissue to place a second segment of the suture against soft tissue. The first segment includes a plurality of first strands coextending axially and having a substantially constant first denier. The second segment has a substantially constant second denier and has a greater number of strands than the first segment such that the second denier is greater than the first denier. The suture further includes a transition zone between the first segment and the second segment. The transition zone includes a first loop formed by two first strands connected to a plurality of second loops, and each second loop is formed by two second strands, such that the transition zone has an increasing denier from the first segment to the second segment. The aspect ratio of the length of each segment and the width of a first strand or a second strand is greater than 100.

This and other embodiments can include one or more of the following features. The method can further include wrapping the first segment around a traction loop before threading the suture. The method can further including cutting the first segment of the suture after the suture is pulled through. The denier of the second segment can be at least twice the denier of the first segment.

In general, in one aspect, a method of manufacturing an integrated suture includes creating a first segment of a yarn, creating a second segment of a yarn, and wrapping a cover over the first and second segments to create a suture. The second segment has a different denier than the first segment, and the first segment and the second segment are created continuously from at least some of the same yarn elements.

In general, in one aspect, a suture includes a polymer monofilament, the polymer monofilament having an end portion and a central portion, the end portion having a smaller denier than the central portion.

In general, in one aspect, a method of manufacturing a suture includes milling an end portion of a polymer monofilament such that the end portion has a smaller denier than a central portion of the monofilament.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings.

FIGS. 1A and 1B show embodiments of a multi-denier yarn.

FIGS. 2A and 2B show embodiments of a multi-denier yarn having three segments.

FIGS. 3A and 3B show embodiments of a multi-denier yarn having a repeating pattern of segments.

FIG. 9A shows an embodiment of a Raschel knitted and cut multi-denier yarn. FIG. 9B shows a process of making the multi-denier yarn of FIG. 9A.

FIG. 13A is an axial cross-section of FIG. 13B.

DETAILED DESCRIPTION

Figure 4A:
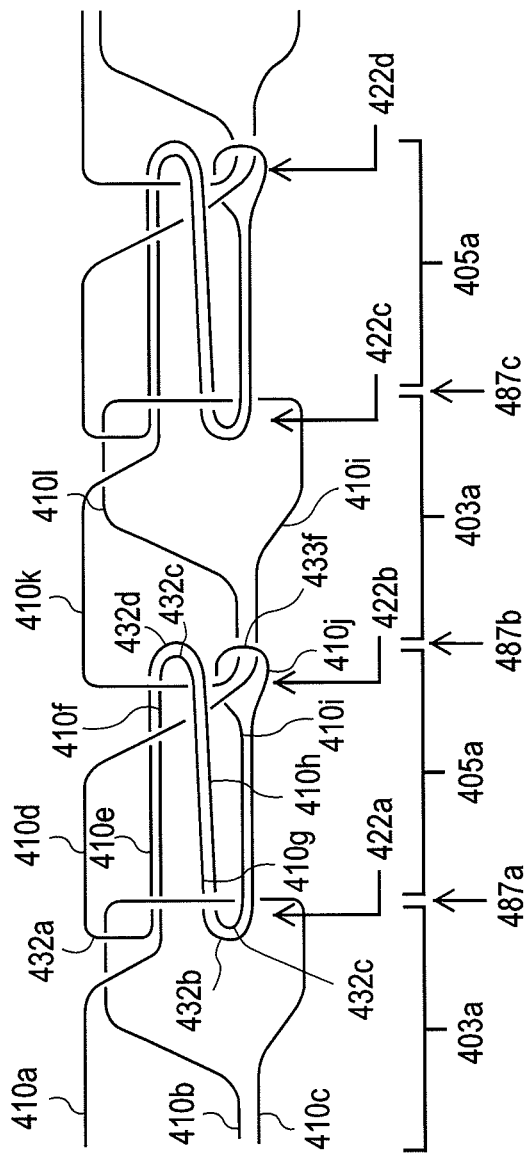
FIGS. 4A and 4B show embodiments of a knitted multi-denier yarn.

Described herein are yarns and sutures having variable deniers.

Referring to FIGS. 1A and 1B, a variable denier yarn 101 can include a low denier segment 103 and a high denier segment 105 having a higher denier than the low denier segment 103. Each segment 103, 105 can include multiple strands 110 coextending axially, i.e. extending substantially along the axis 120 of the variable denier yarn 101. As used herein, the number of strands is the number of yarn element cuts that would be made if a cut were made transversely through the yarn at a particular location. A transition zone 187 can be located at the intersection of, or between, the low denier segment 103 and the high denier segment 105 to transition from the higher denier to the lower denier. For the variable denier yarn 101 of FIGS. 1A and 1B, the transition zone 187 includes a node 122 formed by at least one loop 132 of segment 103 connected to at least one loop 132 of segment 105. Each loop can include a single yarn element, or continuous thread of yarn, looped back approximately 180°.

Referring to FIG. 1A, the denier of the high denier segment 105 can be greater than the denier of the low denier segment 103 because it has more strands 110 than the low denier segment 103. For example, the high denier segment 105 can have at least two times as many strands 110 as the low denier segment 103. Thus, as shown in FIG. 1A, segment 105 can have four strands 110c, 110d, 110e, 110f, while segment 103 can have only two strands 110a, 110b. The node 122 can include a loop 132a formed by strands 110a and 110b connected to a first loop 132b formed by strands 110c and 110f and a second loop 132c formed by strands 110e and 110g. Thus, there are more loops 132 associated with segment 105 than segment 103.

Referring to FIG. 1B, the denier of the high denier segment can be greater than the denier of the low denier segment 103 because the strands 110 of segment 105 can have a greater denier than the strands 110 of segment 103. Thus, there can be an equal number of strands 110 in segment 103 as in segment 105. In the simplest case, as shown in FIG. 1B, segment 103 can include two strands 110a, 110b, and segment 105 can include two strands 110c, 110d. In this embodiment, loop 132a connecting strands 110a and 110b can pass through loop 132b connecting strands 110c and 110d to form the node 122.

A variable denier yarn can include at least one change in denier along its length. Referring to FIGS. 2A and 2B, a multiple-denier yarn 201 includes a high denier segment 205 surrounded by low denier segments 203a, 203b on either side. Transition zones 287 are located at the intersections of the low denier segments 203a, 203b with the high denier segment 205. The transition zones 287 can include nodes 222a, 222b. Each segment can have the same number of loops 232 at node 222a as at node 222b. Although FIGS. 2A and 2B show only three segments with the central segment being the high denier segment, there may be more segments with more than two different deniers and/or there may be only three segments with the central segment being the low denier segment.

As shown in FIGS. 2A and 2B, the high denier segment 205 of variable denier yarn 201 can comprise more strands 210 than the low denier segment 203. Further, each segment 203a, 203b, 205 can include a yarn element that does not extend to adjacent segments. Thus, the variable denier yarn 201 can be manufactured in a way such that it includes yarn elements that do not extend the entire length of the yarn.

Referring to FIG. 2A, the strands 210c, 210e, 210d, 210f of segment 205 can all be formed of the same yarn element. Further, segments 203a, 203b can each include strands 210a, 210b and 210g, 210h formed of different yarn elements than segment 205. Therefore, in the embodiment of FIG. 2A, no yarn elements cross the transition zones 287. The strands 210c, 210e, 210d, 210f of segment 205 can be connected together at a point 230, for example with a knot.

Referring to FIG. 2B, variable denier yarn 201 can include a yarn element that crosses through one or more transition zones to form strands of different segments. For example, as shown in FIG. 2B, a single yarn element can form strands 210a, 210d-h, and 210i. However, segments 203a, 203b can still each include strands 210b, 210c and 210j, 210k, respectively, formed of different yarn elements.

In some embodiments, the variable denier yarn includes a repeating pattern of segments. For example, referring to FIGS. 3A and 3B, the variable denier yarn 301 can include a pattern of alternating low denier segments 303 and high denier segments 305. Each segment can be separated by a transition zone 387. The transition zone 387 can include a node 322 connecting loops of adjacent segments. The high denier segments 305 can each include at least two loops at opposing nodes 322. There can be at least two low denier segments 303 and at least two high denier segments 305 arranged in an alternating pattern.

Referring to FIG. 3A, each segment can be formed of its own yarn element connected together at a point 330. In other embodiments, one or more yarn elements can continue throughout the entire variable denier yarn 301, i.e. through the transition zone 387, to create all of the segments. For example, as shown in FIG. 3B, two yarn elements 340 and 342 can form all of the strands of each segment.

Figure 4B:
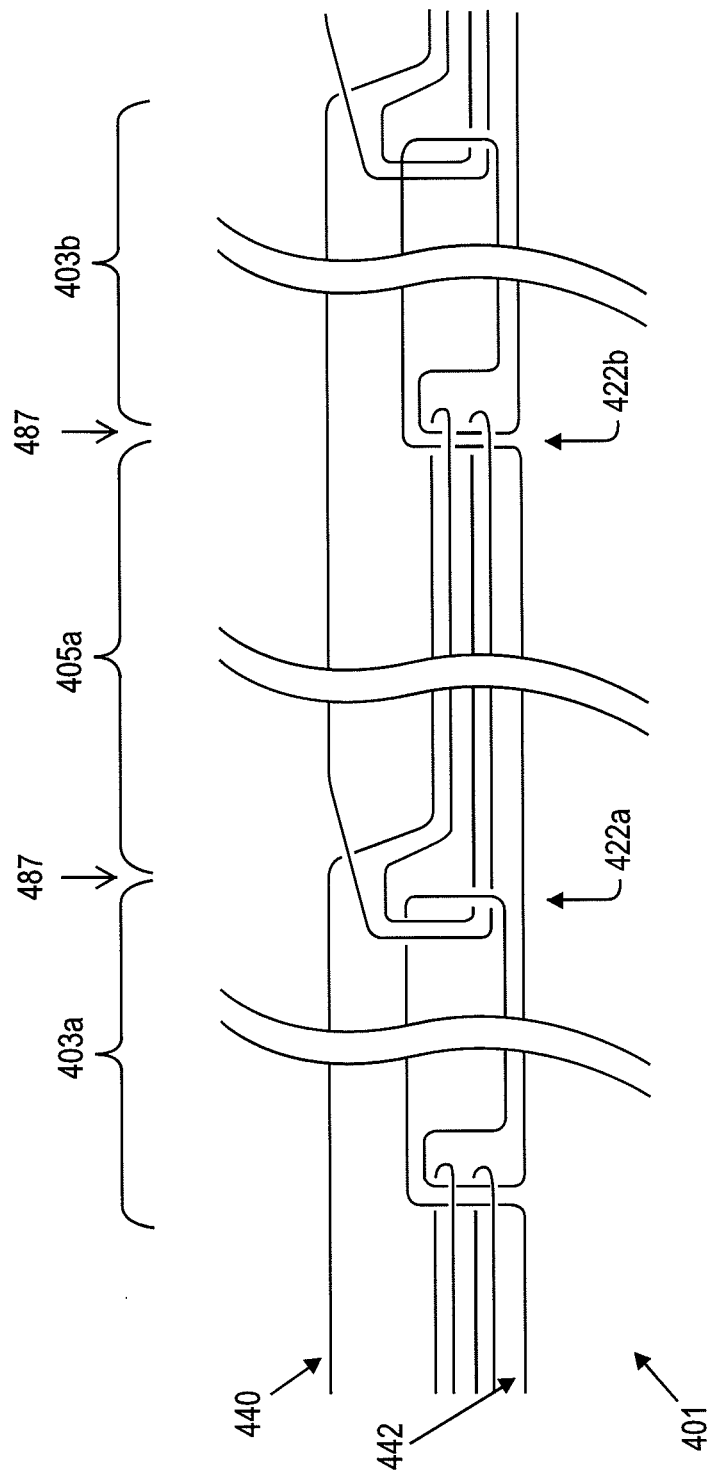

Referring to FIGS. 4A and 4B, the variable denier yarn 401 can be knitted, i.e. fabricated from successive inter-looping of yarn elements. Thus, each yarn element can extend the entire length of the multi-denier yarn 401.

Referring to FIG. 4A, a multi-denier yarn 401 can be formed from a single yarn element. Thus, as shown in FIG. 4A, the low denier segments 403 can include a lower number of strands 410 than the higher-denier segments 405. For example, the low denier segments 403 can include three strands 410 while the high denier segments can include seven strands 410. The low denier segments 403 and the high denier segment 405 can be separated by a transition zone 487a, b, c, which each includes a nodes 422. Further, the high denier segments 405 can include at least two loops at opposing nodes 422 as well as at least one strand that passes through each transition zone 487a, b, c. For example, segment 405a includes three loops 432a, 432b, 432c at node 422a and three loops 432d, 432e, 432f formed at node 422b. Further, strand 410a crosses through the transition zone 487a to form strand 410f. Likewise, strand 410d crosses the transition zone 487b to form strand 410i. Although only two low denier segments 403 and two high denier segments 405 are shown in FIG. 4A, there can be different number of segments, which can be in a repeating pattern.

Referring to FIG. 4B, a multi-denier yarn 401 can be formed from multiple yarn elements. For example, as shown in FIG. 4B, two yarn elements 440 and 442 can each extend along the length of the multi-denier yarn 401.

Figure 5A:
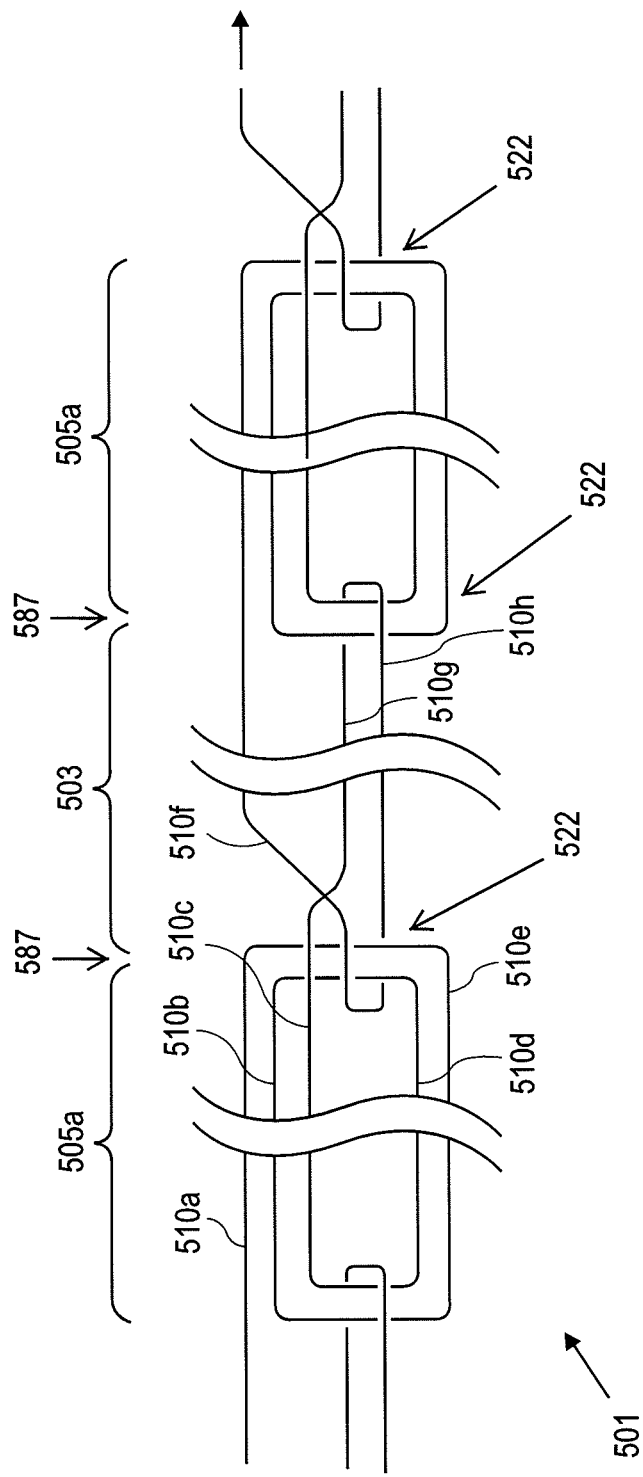
FIGS. 5A and 5B show embodiments of a woven multi-denier yarn.
Figure 5B:
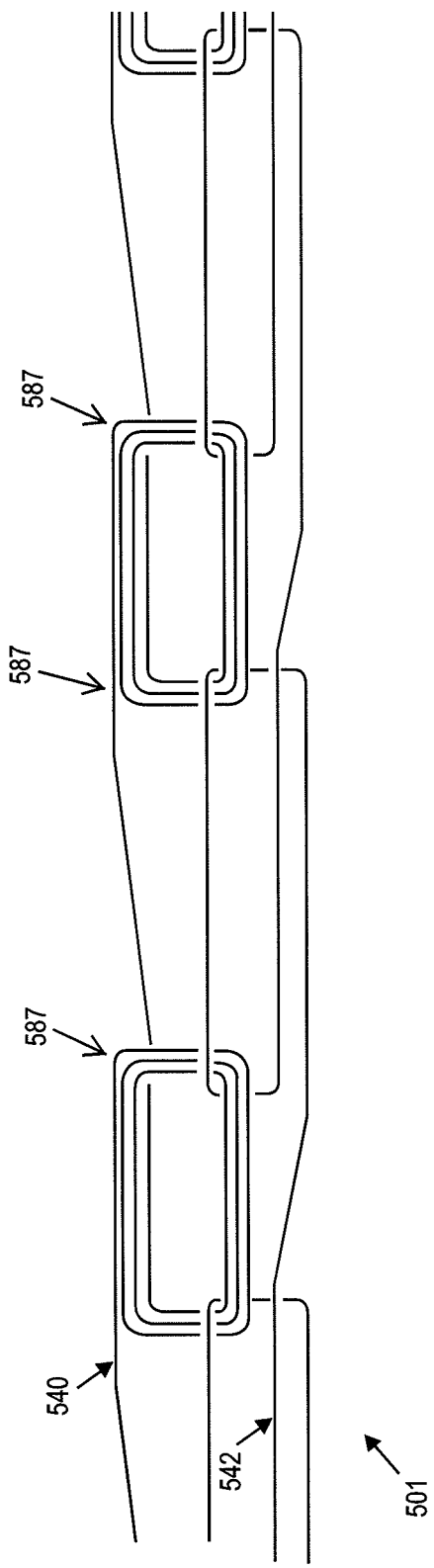

Referring to FIGS. 5A and 5B, the variable denier yarn 501 can be woven, i.e. fabricated by passing a bobbin around a yarn element rather than by pulling a loop around a yarn element. Thus, during weaving, the bobbin carries the end of the yarn element, whereas during knitting and crocheting, the loop around a yarn element does not include the end of the yarn element. Again, each yarn element can extend the entire length of the multi-denier yarn 501.

Referring to FIG. 5A, the multi-denier yarn 501 can be formed from a single yarn element. A yarn element can include a group of subelements running parallel but not integrated together as a textile. The higher-denier segments 505 can have more strands than the low denier segments 503. For example, the low denier segments 503 can include three strands 510 while the high denier segments can include five strands 510. The transition zone 587 can include a node formed by at least one loop of segment 503 connected to at least one loop of segment 505. Further, the high denier segments 505 can include at least two loops at opposing nodes 522 as well as at least one strand that passes across each node 522. Although only two high denier segments 505 and one low denier segment 503 are shown in FIG. 5A, there can be a different number of segments, which can be in a repeating pattern.

Referring to FIG. 5B, the multi-denier woven yarn 501 can be formed from multiple yarn elements. For example, as shown in FIG. 5B, two yarn elements 540 and 542 can each extend along the length of the multi-denier yarn 501.

The yarns including two or more yarn elements with alternating engagement, such as those described with reference to FIGS. 3B, 4B, and 5B, can advantageously avoid creating differential lengths of strands within a segment, which can create slack strands in the yarn. This is because in these cases, at a transition zone, the loops of one yarn element engage adjacent opposing loops of a different yarn element. Further, tension on a given yarn element remains constant as the yarn element passes across a transition zone. In two different denier segments, the sum strand tension is equal, for both the single yarn element yarn, and for the multiple yarn element yarn. Yet, for any strand that crosses the transition zone, the tension is the same throughout the strand spanning both segments. The strand tension is constant for each strand that crosses a transition zone, regardless of which segment it is in. Therefore, for the cases in FIGS. 3B, 4B, and 5B there must be equal tensions on the two opposing arms of all loops. Thus there is no pulley effect where opposing loops cross one another, and no tendency to develop slack strands that cause tangling in the course of manufacture. Moreover, the two yarn element embodiment allows the strands to run parallel to one another along the length of the segment, rather than crossing over one another along the length of the segment. The same principles can be extended to a yarn with greater than two yarn elements. In contrast, for a single-yarn-element yarn such as in FIG. 4A, the loops that interface at transition zones have different tensions on the opposing arms of a given loop, because the strand count, with the same yarn element, is different in the different segments. The mean strand tension is different in the different segments, but the strand tension in the strand crossing the transition zone is equal. If the coefficient of friction were nearly zero, there would be pulley slippage where the opposing loops engage each other.

Figure 6:
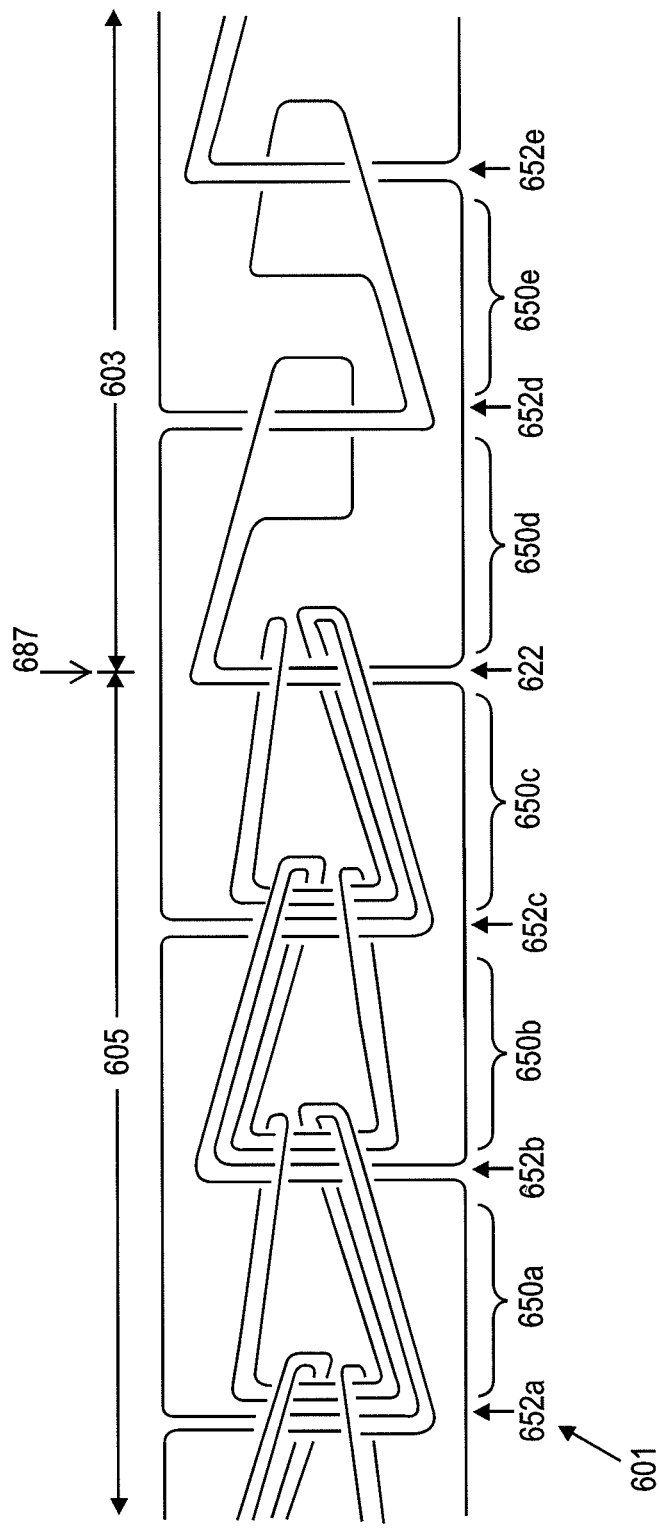
FIG. 6 shows an embodiment of a multi-denier yarn with segments having a plurality of sections.

In some embodiments, one or more segments in a multi-denier yarn can have multiple sections connected by semi-nodes, i.e. loop connections between strands of the same segment such that there is no change in denier. For example, referring to FIG. 6, a multi-denier yarn 601 includes a low denier segment 603 and a high denier segment 605 connected by a transition zone 687 having a node 622. The high denier segment 605 includes a plurality of sections 650 connected by semi-nodes 652. Each section 650a, 650b, 650c of the high denier segment 605 is of equal denier, and each section 650d, 650e of the low denier segment 603 is of equal denier. There can be one, two, or more sections 650 in at least one segment of the multi-denier yarn 601. For example, each segment can include two or three sections. Although the multi-denier yarn 601 shown in FIG. 6 is knit, the yarn 601 can also be woven. A knit multi-denier yarn 601, as shown in FIG. 6, may be advantageous to achieve close semi-node spacing.

Figure 7A:
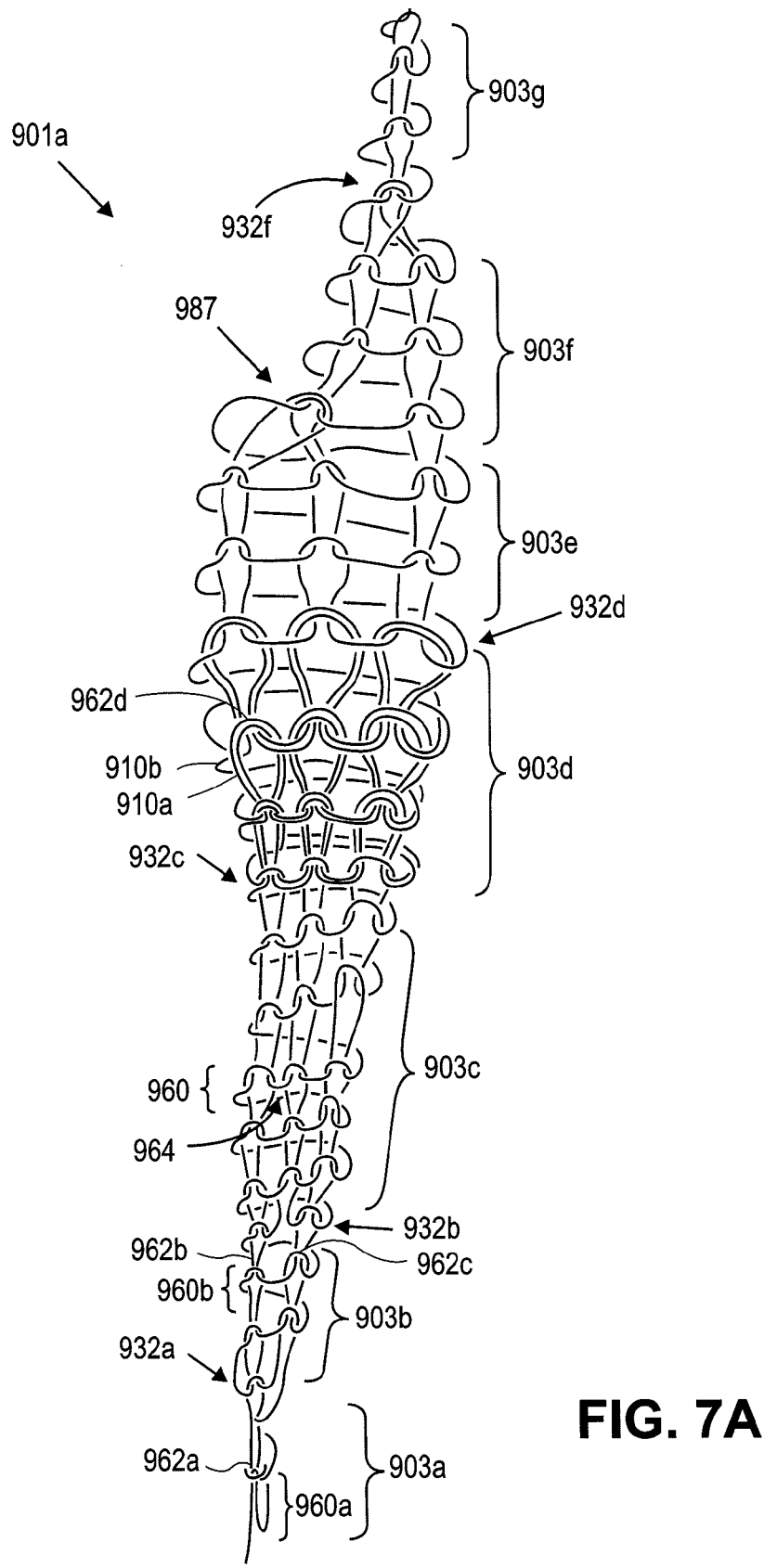
FIGS. 7A and 7B show embodiments of a linear knitted yarn.
Figure 7B:
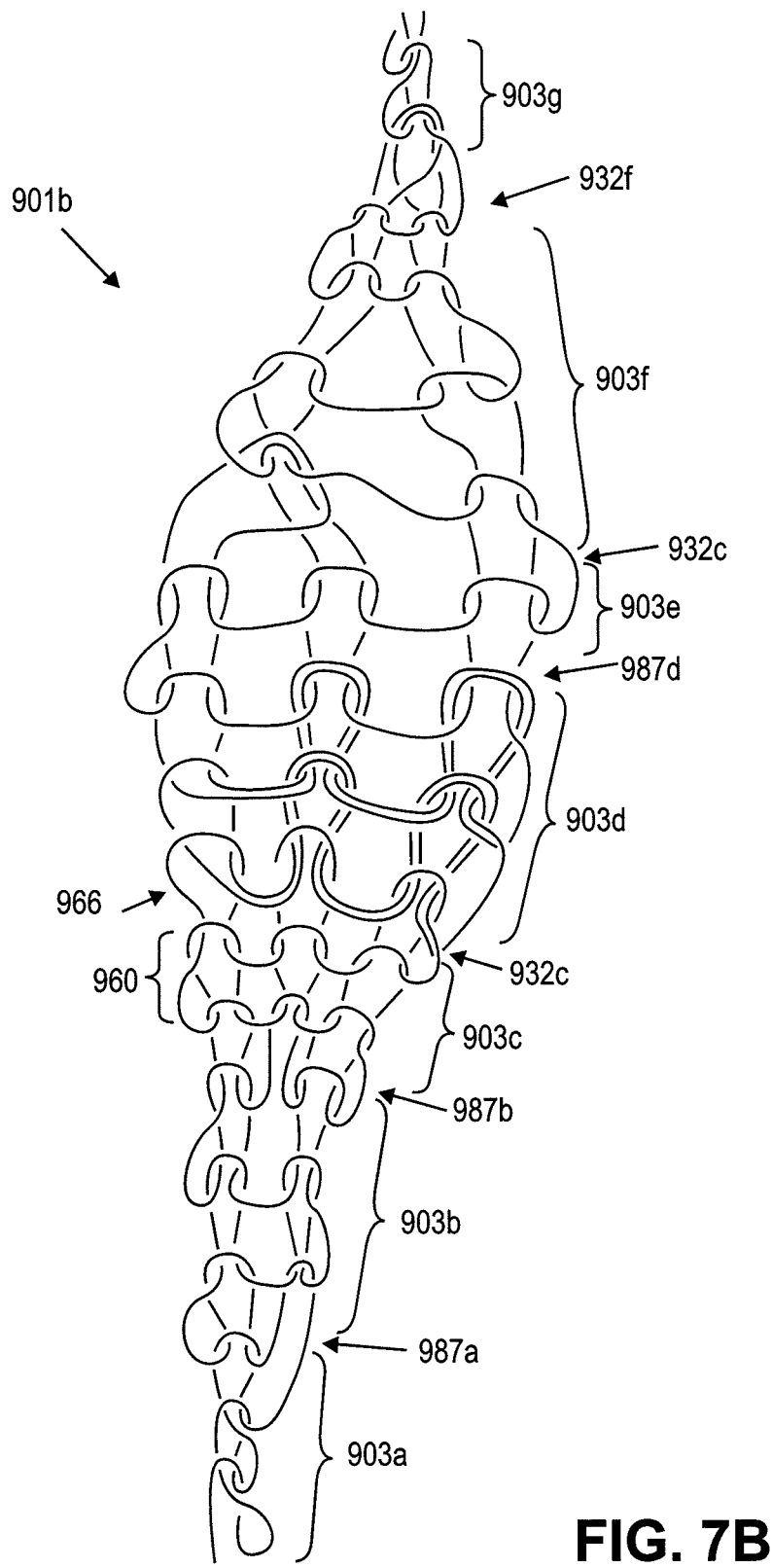

In some embodiments, shown in FIGS. 7A and 7B, a multi-denier yarn can be constructed as an elongate or linear weft knitted structure. Referring to FIG. 7A, a multi-denier yarn 901a can be formed as a linear knitted structure with the progression of yarn extending back to start on the same side on every course or radial row of stitches, advancing to the new row or course. Thus, the yarn 901a can be formed of a plurality of circumferentially-extending courses 960, each course including at least one wale 962 or back-and-forth loop. Each course 960 can include a circumferential strand 964 extending either in front or in back of the course to start the next course, substantially forming a circular knit.

The multi-denier yarn 901a can include at least two segments 903 of different denier connected by nodes 932. The change in denier from one segment 903 to another segment at transition zone 987 can be the result of an increase in the number of strands 910 per segment.

The increase in the number of strands 910 per segment 903 can be caused by an increase in the number of wales 962 per course 960. For example, course 960a of segment 903a includes a single wale 962a, while course 960b of segment 903b includes two wales 962b, 962c. Likewise, each course of segment 903c includes more wales than each course of segment 903b. Alternatively, or in addition, the number of strands 910 per segment 903 can be caused by an increase in the number of strands 910 per wale. For example, segment 903d includes two strands 910a, 910b in a single wale 962d. In one embodiment, the yarn 901 can be made by controlling the raising of the latch needles of a circular knitting machine, e.g., by holding them raised for one or more extra revolutions, then proceeding with the cam one revolution to make the stitches, and again holding them raised for one or more revolutions. The transition zones 987 between each segment can differ depending on the cause of the change in denier as well as the direction of knitting. For example, the increase in denier at node 932b is caused by the formation of an additional loop, the increase in denier at node 932c is caused by looping back over the same course, the decrease in denier at 932d is caused by decreasing the amount of looping back over the same course, and the decrease in denier at 932c and 932f is caused by using a transfer stitch. In each case, however, the change in denier can be associated with a single loop engaging multiple loops, or vice versa, or by a given number of loops engaging a greater or lesser number of loops. In some embodiments, a computerized flat-bed knitting machine, such as a Shima-Seiki, can be used to create transfer stitches to pass the loops of two wales to a single wale in an adjacent course.

Referring to FIG. 7B, a multi-denier yarn 901b can be formed as a flat linear knitted structure with stitches reversing direction along each row of stitches. Thus, the yarn 901b can be formed of a plurality of circumferentially-extending courses 960, each course including at least one wale 962. Each course 960 can include an axially extending strand 966 to start the next course.

Similar to the multi-denier yarn 901a of FIG. 7A, the multi-denier yarn 901b can include at least two segments 903 of different denier connected by transition zones 987. The change in denier from one segment 903 to another segment can be the result of an increase in the number of strands per segment 903, which can be the result of an increase in the number of wales per course or an increase in the number of strands per wale.

Figure 8A:
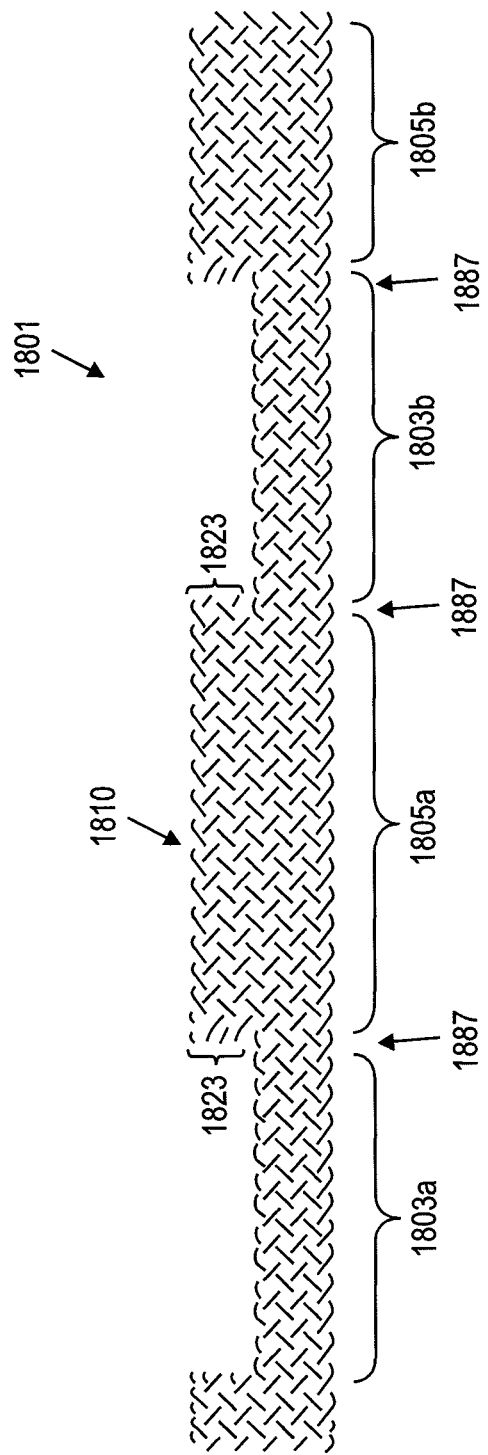
FIG. 8A shows an embodiment of a braided and cut multi-denier yarn.

Referring to FIG. 8A, in some embodiments, a multi-denier yarn 1801 can include segments 1803a,b and segments 1805a,b. Segments 1805a,b can have a greater number of strands than segments 1803a,b such that the segments 1805a,b have a higher denier than segments 1803a,b. The strands 1810 of each segment can be integrated together, such as braided together. Some yarn elements of the high denier segments 1805a,b can terminate at a transition zone 1887 between the high denier segments 1805a,b and the low denier segments 1803a,b. Thus, the transition zone 1887 can include ends 1823 of yarn elements of the higher denier sections 1805a,b that do not extend into the low denier segments 1803a,b. In some embodiments, the ends 1823 can be loose ends, i.e., not attached together. In other embodiments, the ends 1823 can be attached together, such as with a glue or by melting.

Figure 8B:
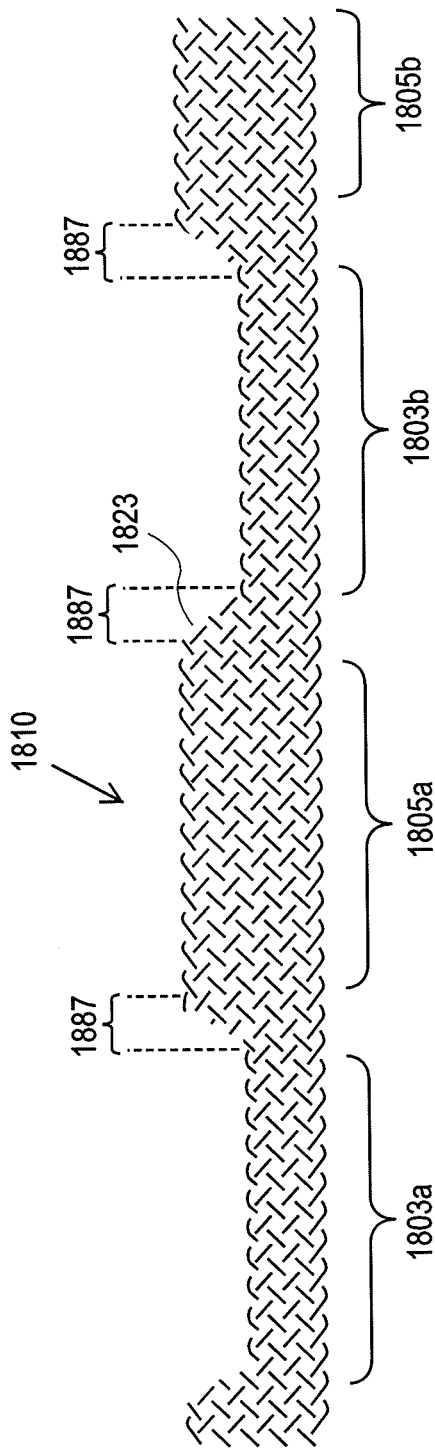
FIG. 8B shows an embodiment of a braided and cut multi-denier yarn having a gradual change in denier.

As shown in FIG. 8A, the ends 1823 can all be aligned transversely to the axis of the multi-denier yarn such that there is a sudden change in denier at the transition zone 1887. In another embodiment, the array of ends 1823 can be aligned oblique to the yarn axis so as to create a more gradual change in denier from the low denier segments 1803*a,b* to the high denier segments 1805*a,b* at the transition zone 1887, as shown in FIG. 8B. The yarn elements forming the strands of the low denier segments 1803*a,b* can extend into neighboring segments 1805*a,b* to form strands of the high denier segments 1805*a,b*.

In some embodiments, the strands in each segment are braided together in a tubular braid. In other embodiments, the strands of the high denier segments 1805*a,b* are braided together in a tubular braid while the strands of the low denier segments 1803*a,b* are braided together in a flat braid. In still other embodiments, the strands in each segment are braided together in a flat braid.

Figure 8C:
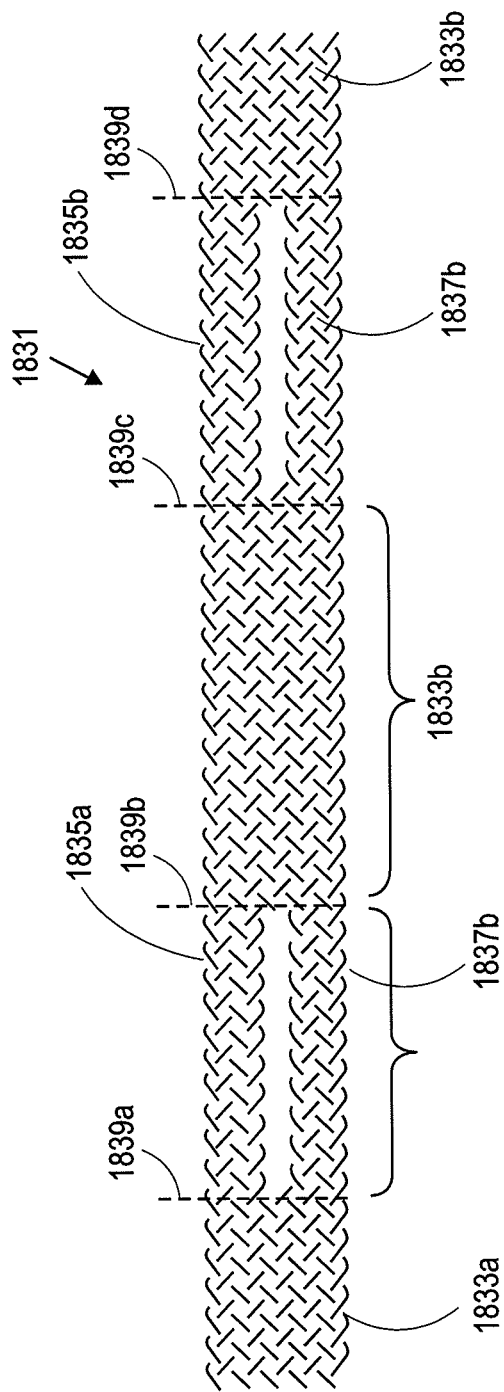
FIG. 8C shows a process of making the multi-denier yarn of FIG. 8B.

Referring to FIG. 8C, the multi-denier yarn 1801 of FIG. 8A can be formed from a yarn 1831 having a single braid section 1833 that divides into two or more parallel unitary braids 1835, 1837 and then joins back into a single unitary braid 1833 again. One or more of the parallel braids 1835, 1837 can then be cut at the splits 1839. The remaining parallel braid 1835, 1837 can form the lower-denier segment 1803 of the multi-denier yarn 1801, while the unitary braid 1833 can form the higher-denier segment 1805.

Referring to FIG. 9A, in some embodiments, a multi-denier yarn 1901 can include segments 1903*a,b* and segments 1905*a,b,c*. Segments 1905*a,b* can have a greater number of strands than segments 1903*a,b* such that the segments 1905*a,b* have a higher denier than segments 1803*a,b*. The strands 1910 of each segment can be knitted together in a warp knit, such as a raschel knit, crocheted together, or knitted together with parallel pillar stitches and weft inlays. Some yarn elements of the high denier segments 1905*a,b* can terminate at a transition zone 1987 between the high denier segments 1905*a,b* and the low denier segments 1903*a,b*. Thus, the transition zone 1987 can include ends 1923 of yarn elements of the higher denier sections 1905*a, b* that do not extend into the low denier segments 1903*a,b*. The yarn elements forming the strands of the low denier segments 1903*a,b* can extend into neighboring segments 1905*a,b* to form strands of the high denier segments 1905*a,b* as well.

Referring to FIG. 9B, the multi-denier yarn 1901 of FIG. 9A can be formed from a yarn 1931 having a full raschel knit section 1933 that is cut at splits 1939 to form high denier segments 1905 and low denier segments 1903.

Figure 10A:
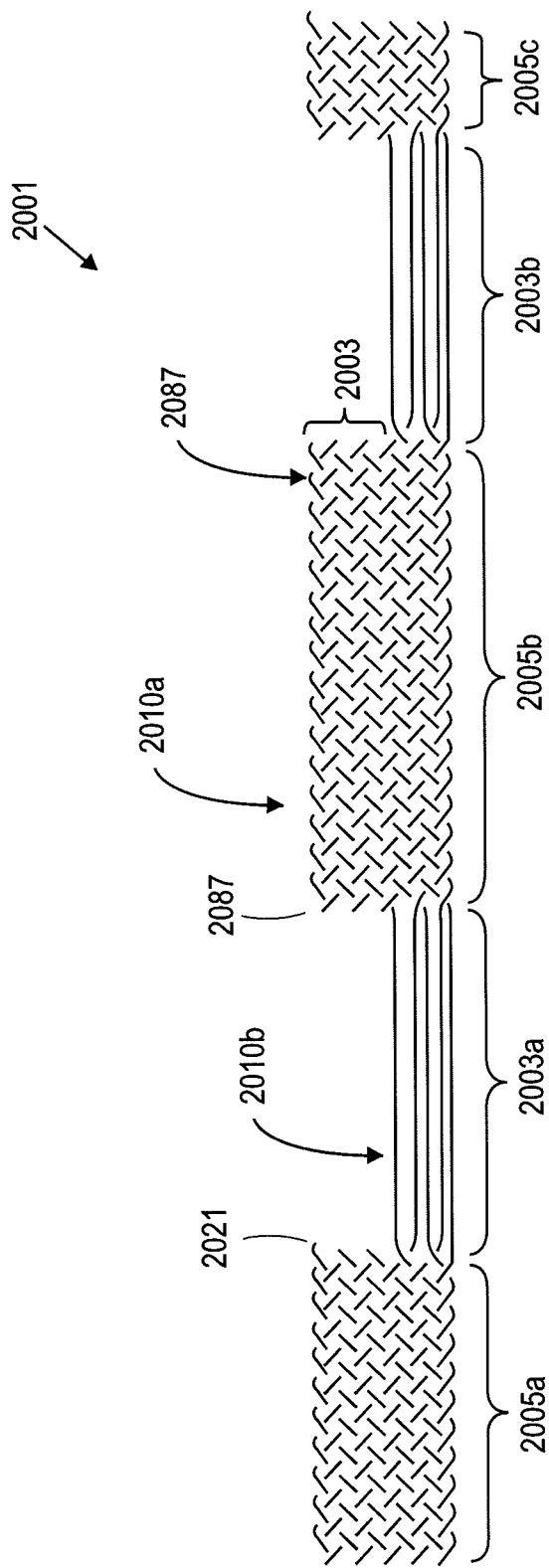
FIG. 10A shows an embodiment of a multi-denier yarn having braided and unbraided portions.
Figure 10B:
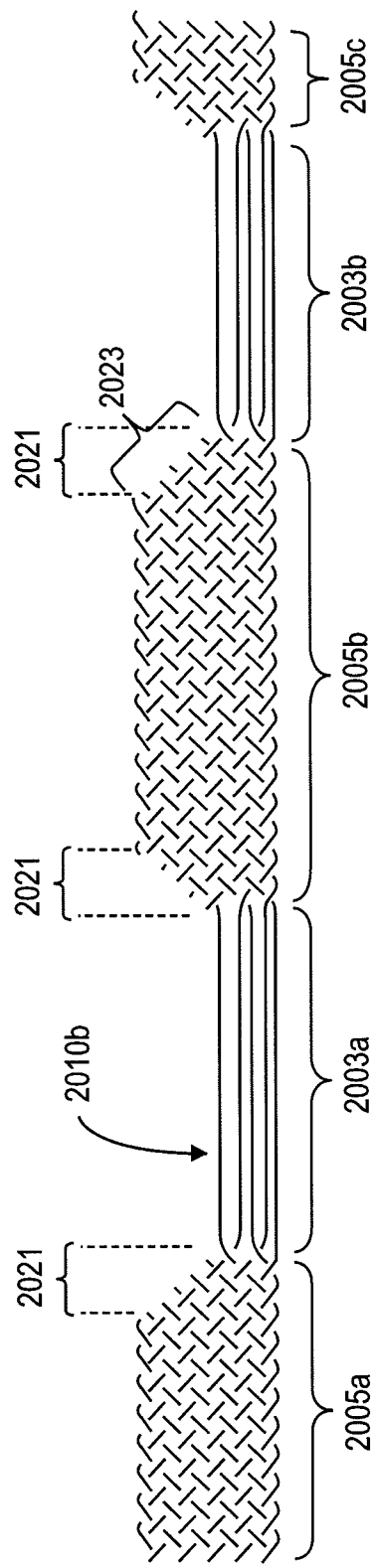
FIG. 10B shows an embodiment of a multi-denier yarn having braided and unbraided portions and having a gradual change in denier.

Referring to FIG. 10A, in some embodiments, a multi-denier yarn 2001 can include segments 2003*a,b* having a lower denier than segments 2005*a,b*. The higher-denier segments 2005*a,b* can include strands 2010*a* of yarn integrated together, such as in a tubular or flat braid, a tubular or flat braid with longitudinal warp fibers, a warp knit, or a weave with warp and weft yarn elements. In contrast, the lower-denier segments 2003*a,b* can include strands 2010*b* extending substantially parallel to one another and the axis of the yarn 2001, i.e. can be not braided, knit, or woven. Some yarn elements of the high denier segments 2005*a,b* can terminate at a transition zone 2087 between the high denier segments 2005*a,b* and the low denier segments 2003*a,b*. Thus, the transition zone 2087 can include ends 2023 of yarn elements of the higher denier sections 2005*a, b* that do not extend into the low denier segments 2003*a,b*. As shown in FIG. 10A, the ends 2023 can all be aligned transversely to the axis of the multi-denier yarn such that there is a sudden change in denier at the transition zone 2087. In another embodiment, the ends 2023 can be aligned diagonally so as to create a gradual change in denier from the low denier segments 2003*a,b* to the high denier segments 2005*a,b*, as shown in FIG. 10B. The yarn elements forming the strands of the low denier segments 2003*a,b* can extend into neighboring segments 2005*a,b* to form strands of the high denier segments 2005*a,b*.

Figure 10C:
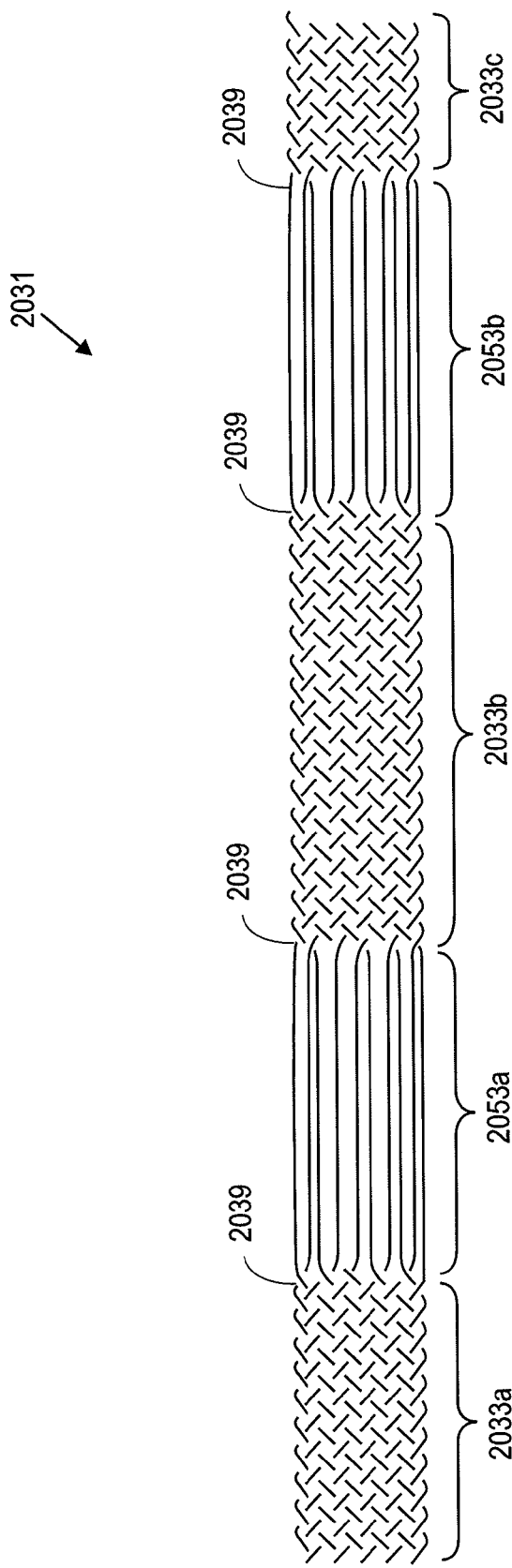
FIG. 10C shows a process of making the multi-denier yarn of FIG. 10A.

Referring to FIG. 10C, the multi-denier yarn 2001 of FIG. 10A can be formed from a yarn 2031 having a single braided section 2033, an unbraided section 2053, and then another braided section 2033. The yarn elements can be cut at the splits 2039 to form the lower-denier segments 2003 and the high denier segments 2005.

In some embodiments, a multi-denier yarn as described with respect to FIGS. 8 through 10 can include, in addition to yarn elements that are braided or knit, warp yarn elements running longitudinally that run through the braided or knit portions but are not themselves braided or knit. These warp yarn elements may be included throughout the yarn cross section or may be located in only portions of the yarn cross section.

Figure 11:
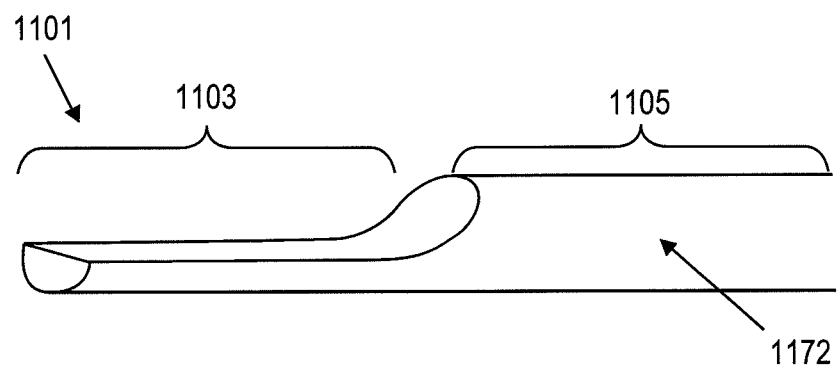
FIG. 11 shows an embodiment of a multi-denier monofilament suture.

Referring to FIG. 11, in some embodiments, a multi-denier yarn 801 can be formed of a single monofilament 872, such as a polymer monofilament. The multi-denier yarn can thus include a low denier segment 803 having a smaller denier than a high denier segment 805. The smaller denier segment 803 can be formed by removing a portion of the monofilament, such as through milling.

In embodiments of the multi-denier yarns described herein, the aspect ratio of the distance between segments of different denier and the width of a yarn element is greater than 100, such as greater than 200, greater than 500, or greater than 1,000. For example, the distance between segments of different denier can be between 5 and 100 cm. In some embodiments, each transition zone is substantially equidistant. In other embodiments, each segment of the same denier has the same length. In yet other embodiments, repetition of transition zones between repeating segments is at regular intervals. Moreover, where the multi-denier yarns described herein change in denier, the change can be greater than 10%, such as by a factor of two or more.

In some embodiments, the distance between transition zones can be short, e.g., 5-10 mm, so that the yarn includes a large number of segments. In other embodiments, the distance between transitions zones can be long, e.g. 10-50 cm apart, so that yarn includes only a few, e.g., less than 10, such as only two, different segments.

In embodiments of the multi-denier yarns described herein, the yarn includes one or more low denier segments and one or more high denier segments. Further, additional segments having a denier between the deniers of the low denier segments and the high denier segments can be present.

In embodiments of the multi-denier yarns described herein, each segment can have a substantially constant denier, i.e., can change by less than 5%, such as less than 1%, along the length of the segment. Further, the transition zones can include a sudden change in denier or can have a gradual change in denier, e.g., include a gradual decrease in the number of wales per course. Stated differently, the yarn can have a change in denier over a length being as shorter than 0.5% of the higher denier segment, or as long as 50% of the length of the higher denier segment, or can have gradually increasing and decreasing denier in a single length of yarn or in a repeating pattern over the length of the yarn.

In embodiments of the multi-denier yarns described herein, all of the yarn elements are made of the same denier and material. In other embodiments, at least one yarn element is made of a different denier or material. The yarn elements can be made of a material such as polyester, polyethylene, or polypropylene. Further, the multi-denier yarn can be substantially inelastic, e.g., the multi-denier yarn can be configured to rupture with less than 5% axial elastic strain.

Advantageously, the multi-denier yarns described herein can be made using an automated process without interrupting the linear continuity of the yarn and producing a repeating pattern of varying denier. In some of the embodiments of the multi-denier yarns described herein, standard commercial machinery can be used to manufacture the sutures. For example, the yarns described herein can be manufactured using a Shima Seiki SWG 041N machine, a Herzog LZ2 series machine, a Herzog NG2 series machine, a Comez DNB-800 machine for narrow nets, a Double Bar Raschel machine HDR8, or a Karl Mayer Double needle bed warp knitting machine.

Figure 12A:
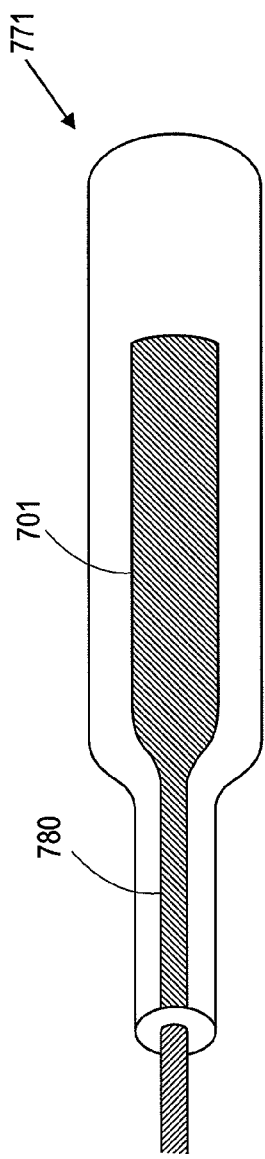
FIGS. 12A-12C show a composite structure including a multi-denier yarn.

Any of the multi-denier yarns described herein can be used independently as a completed textile, or as part of a composite or integrated structure, which in turn functions as a variable denier yarn or completed structure. For example, referring to FIGS. 12A-12C, an integrated structure 771 can include an outer thread 780 braided or wrapped around one or more of the multi-denier yarns 701 such that the multi-denier yarn acts as an axial center of the integrated structure 771. Alternatively, an integrated structure could be made by braiding or winding one or more multi-denier yarns together. The independent or composite structure can be, for example, a suture for use in surgical procedures, without further modifications other than cutting it into lengths for use, tipping, etc.

Figure 12B:
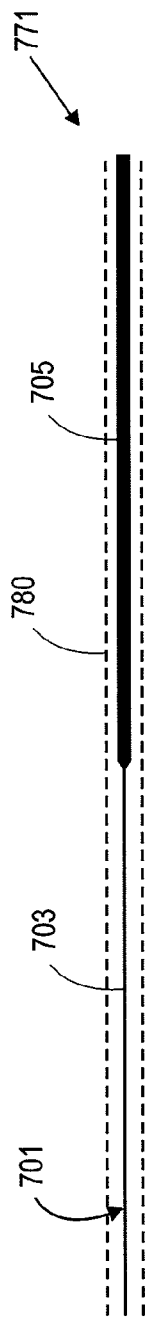
Figure 12C:
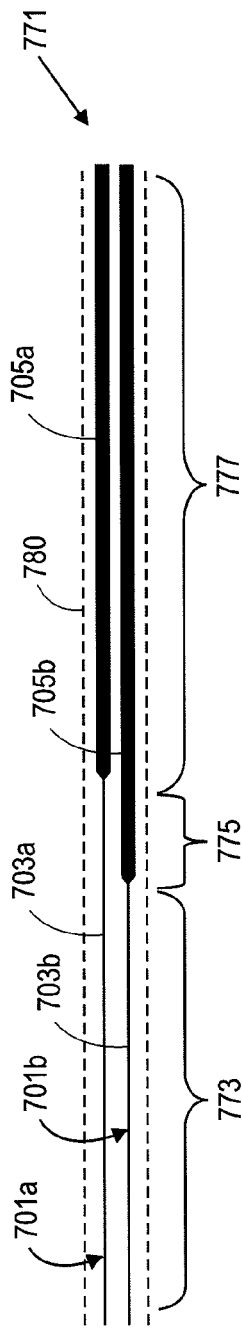

Referring to FIG. 12B, a single multi-denier yarn 701 can be wrapped or braided in an outer thread 780. In contrast, referring to FIG. 12C, the composite structure 771 can include multiple multi-denier yarns 701a, 701b wrapped or braided in an outer thread 780. As shown in FIG. 12C, the high denier portions 705a, 705b of the multi-denier yarns 701 can be staggered axially so as to create three sectors 773, 775, 777 of variable denier along the composite structure 771. That is, where the high denier segments 705a, 705b line up axially, the denier of the sector 777 will be greater. At the staggered portion (sector 775), the denier of sector 775 will be lower, and where the low denier segments align (at sector 773), the composite 771 will have an even lower denier. Further, referring to the yarns 901a, 90b of FIGS. 7A and 7B, the transition zones may be knitted so that they are staggered along the length of the suture to avoid having a lump in the yarn caused by having multiple transition zones positioned at the same axial location.

Figure 13A:
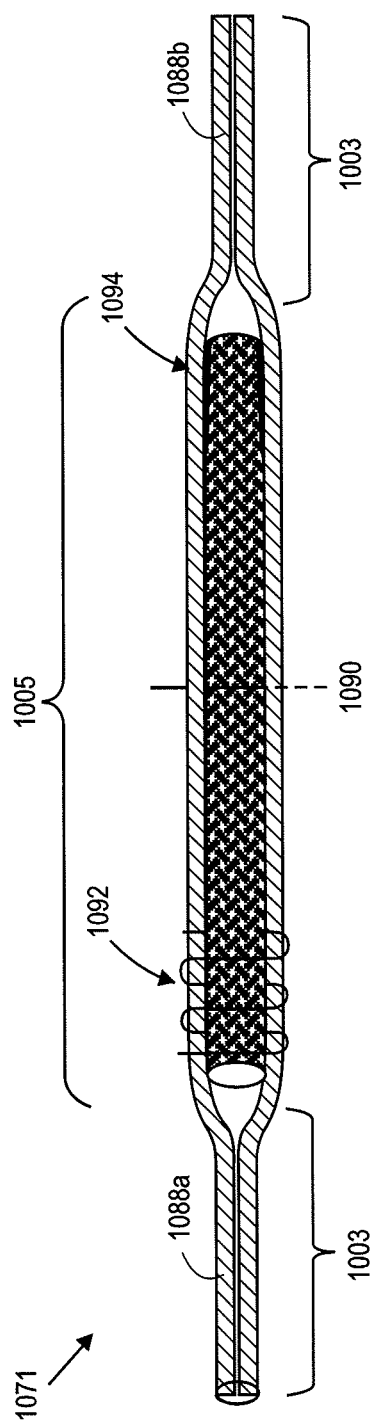
FIGS. 13A-13B show an embodiment of a variable denier surgical suture.
Figure 13B:
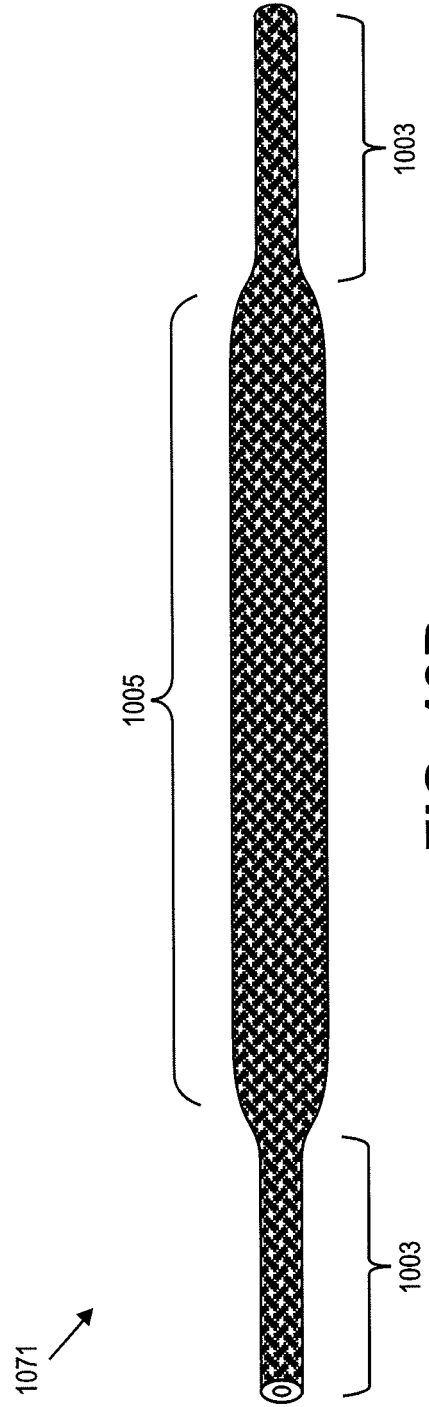

Referring to FIGS. 13A and 13B, an integrated structure 1071 can be formed of single-denier inner element 1082 introduced by textile process inside an outer thread 1084. The single-denier inner element 1082 can have a shorter length than the outer thread 1084 to as to create a segment 1005 of greater denier than an adjacent segment 1003. In one embodiment, the integrated structure 1071 can be formed by knitting, braiding, or weaving one structure over the other. In another embodiment, the composite structure 1071 can be formed by introducing the single-denier inner element 1082 into the radial center of the outer element 1084. Additionally, the inner element 1082 and outer element 1084 can be supplementally secured by sewing one or more stitches 1092 and/or by use of adhesive 1094. If an integrated structure 1071 is produced with an inner element 1082 having a length longer than the desired final length, one or both ends 1088a, 1088b of the outer element 1084 can be pulled towards the axial center 1090 of the composite structure 1071 to expose the inner element 1082, and then desired amount of the inner element 1082 can be removed. An alternative way to remove part of the inner element 1082 is to introduce a thin cutting tool inside the tube of the outer element 1084, to the depth where the inner thread is to be cut, and cutting it off with the tool, and then removing the unwanted portion of inner thread.

Figure 14A:
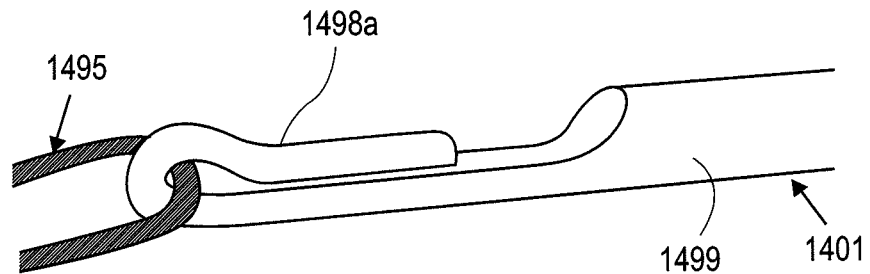
FIGS. 14A-14B show use of a multi-denier suture.
Figure 14B:
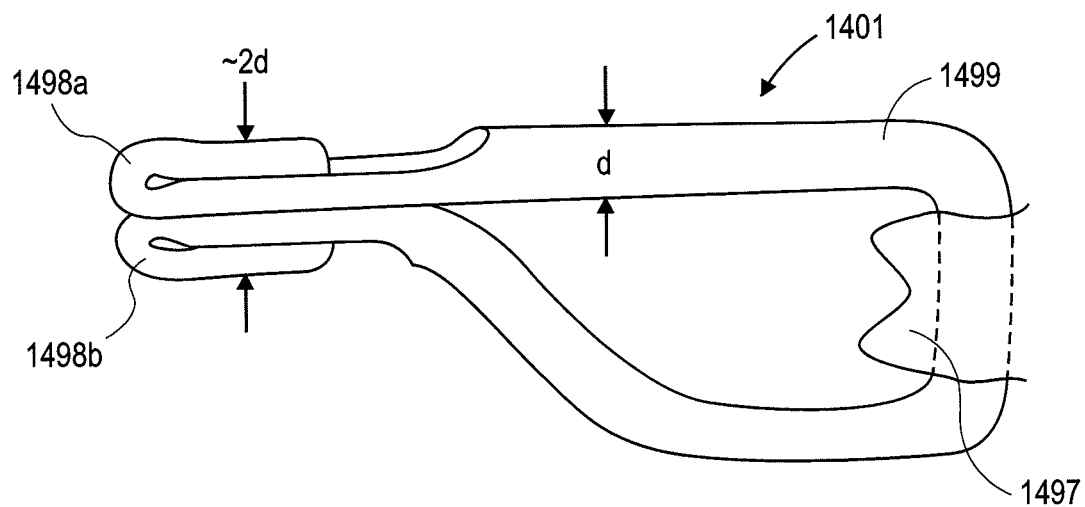

The structures described herein can advantageously be used as a suture during surgical procedures. Referring to FIG. 14A, the low denier portions 1198 can be at the ends of the suture 1101, allowing the suture 1101 to be wrapped around a traction loop 1195 so as to be more easily threaded through a small opening in a surgical instrument, surgical implant, or suture lock. For example, the ends 1198 of the suture 1101, when folded together, can have an equivalent or smaller diameter of the central portion 1199 of the composite structure. In use, therefore, the low denier portions 1198 can be placed straight or looped through a small opening, and traction can be applied to the low denier portion 1198 such that the low denier portion 1198 is first pulled through the hole. Then the high denier central portion 1199 is pulled through the opening, more nearly filling the entire dimension of the hole. Further, referring to FIG. 14B, in use, the high denier central portion 1199 can be placed against soft tissue 1197 being repaired. The lower-denier ends 1198a, 1198b can later be cut off and removed. Having the high denier portion against the tissue, with greater side profile, can advantageously increase the stability of the suture in the tissue. The suture 1101 can be any of the multiple-denier sutures described herein.

Moreover, the structures described herein can be used for other applications. In one embodiment, a vascular graft is formed from a multi-denier yarn as shown in FIG. 8C. That is, the graft can divide from a singular tubular structure into two or more tubular structures. The graft can be made by continuous seamless braiding, such as with a Herzog VF 1/(4-32)-140 S Variation Braiding Machine.

What is claimed is:

1. A suture, comprising:
   a first segment of suture comprising a plurality of first strands, the first segment having a substantially constant first denier; and
   a second segment of suture comprising a plurality of second strands, the second segment having a substantially constant second denier;
   wherein the first and second segments are aligned along a longitudinal axis of the suture;
   wherein there are more second strands in the second segment than first strands in the first segment such that the second denier is greater than the first denier;
   wherein a first portion of the plurality of second strands is made from a first plurality of yarn elements that extend through the first segment and the second segment, and wherein a second portion of the plurality of second strands is made from a second plurality of yarn elements that are present in the second segment and not the first segment, the first portion integrated around the second portion; and
   wherein ends of the second plurality of yarn elements are positioned along an axis that is oriented substantially transverse to the longitudinal axis.

2. The suture of claim 1, wherein the first portion of the plurality of second strands are braided, knitted, or woven together.

3. The suture of claim 2, wherein the plurality of first strands are braided, woven, or knitted together in a continuous element with the first portion of the plurality of second strands.

4. The suture of claim 1, wherein ends of the strands in the second plurality of yarn elements are loose in a transition zone between the first segment and the second segment.

5. The suture of claim 1, wherein the second denier is at least twice as large as the first denier.

6. A method of suturing, comprising:
- threading a first segment of a suture through an opening of a surgical instrument, wherein the first segment comprises a plurality of first strands, the first segment having a substantially constant first denier; and
- pulling the suture through tissue to place a second segment of the suture against soft tissue, wherein the second segment comprises a plurality of second strands, the second segment having a substantially constant second denier;
- wherein the first and second segments are aligned along a longitudinal axis of the suture;
- wherein there are more second strands in the second segment than first strands in the first segment such that the second denier is greater than the first denier; and
- wherein a first portion of the plurality of second strands is made from a first plurality of yarn elements that extend through the first segment and the second segment, and wherein a second portion of the plurality of second strands is made from a second plurality of yarn elements that are present in the second segment and not the first segment, the first portion integrated around the second portion wherein ends of the second plurality of yarn elements are positioned along an axis that is oriented substantially transverse to the longitudinal axis.

7. The method of claim 6, further comprising wrapping the first segment around a traction loop before threading the suture.

8. The suture of claim 1, wherein the first strands and the second portion of the plurality of second strands form the radially inner-most elements of the textile yarn.

9. The suture of claim 1, wherein the first portion of the plurality of second strands form a tubular overbraid around the second portion of the plurality of second strands.

10. The suture of claim 1, further comprising at least one third yarn element, the third yarn element extending through the first and second segment, the first portion integrated around the third yarn element.

11. The suture of claim 10, wherein there are a plurality of third yarn elements, and wherein at least some of the plurality of third yarn elements are integrated together within the second segment and not within the first segment.

12. The method of claim 6, wherein threading the first segment of a suture through an opening comprises looping the first segment through the opening such that the first segment folds upon itself.

13. The method of claim 12, wherein the folded first segment, when placed or pulled with a traction loop through a small opening, has an equivalent or smaller diameter than the second segment.

14. A method of manufacturing a suture, comprising:
- braiding a plurality of strands together into a tubular braid;
- introducing a constant denier segment into a radial center of the tubular braid such that a textile yarn having a first segment and a second segment is formed, the second segment having a greater denier than the first segment;
- introducing a plurality of additional constant denier segments into the radial center of the tubular braid such that a plurality of first segments and a plurality of second segments are formed, the first and second segments arranged in an alternating pattern along the length of the textile yarn; and
- cutting the textile yarn such that a plurality of sutures having a first segment and a second segment are formed.

15. The method of claim 14, wherein the braiding and introducing steps are continuous and uninterrupted.

* * * * *